June 28, 1949. A. KREBS Plant Pat. 850
ROSE PLANT
Filed Dec. 17, 1947
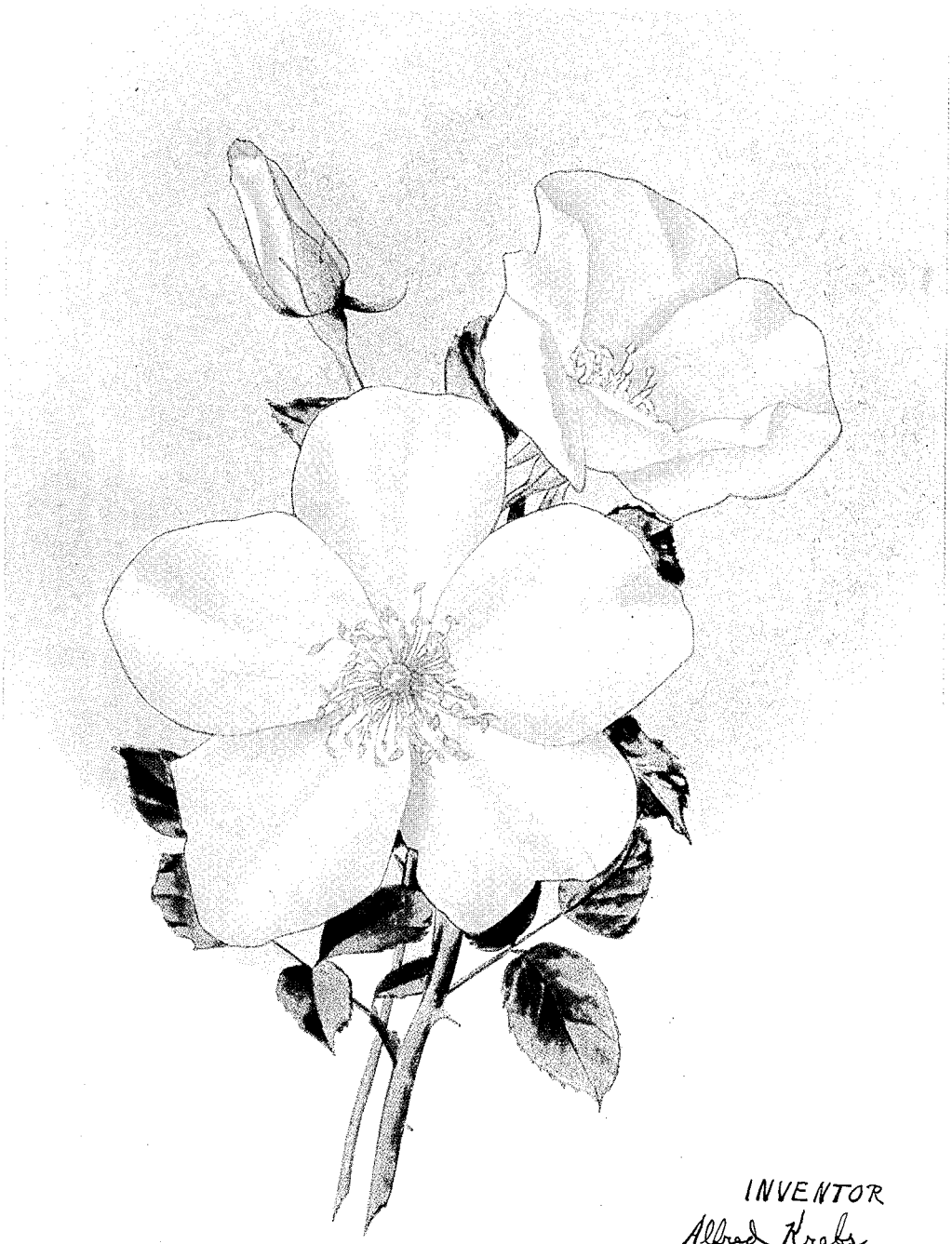
INVENTOR
Alfred Krebs
By Orville M. Kile
Plant Pat. Agt.

Patented June 28, 1949

Plant Pat. 850

UNITED STATES PATENT OFFICE

850

ROSE PLANT

Alfred Krebs, Montebello, Calif., assignor to
Howard & Smith, Montebello, Calif.

Application December 17, 1947, Serial No. 792,237

1 Claim. (Cl. 47—61)

My present invention relates to a new and improved variety of single hybrid tea rose plant. It was produced by me from a cross of two unnamed seedlings which in turn had been produced by me.

This new variety is of the same type as the variety Dainty Bess but has a pure white flower and is a much stronger grower. Other outstanding qualities of the new variety are its large well-branched bloom heads or trusses and its habit of continuously blooming from eary spring to advent of winter frosts. This combination of qualities makes it especially good when closely planted for use in hedges and for landscape effects as a border to taller growing roses, although single isolated specimens are also very effective.

The accompanying illustration shows a bud, a partly opened flower and a newly full-blown flower, together with portions of stems and foliage.

Following is a detailed description of the plant and flower of this new variety. Any reference to colors indicates the ordinary dictionary meaning of the term.

*The plant*

Growth: Compact strong grower, producing large well-formed heads of bloom.

Blooming habit: Continuous bloomer, bearing a large quantity of flowers from eary spring to winter frosts.

Disease resistance: In our climate this variety is practically immune to all diseases common to roses.

Stems:
- *Color.*—Pale green.
- *Strength.*—Substantial.
- *Rigidity.*—Stiff and upright.
- *Thorns.*—Few, brown, sharp, medium sized, pointed at right angles.

Foliage: Leaflets, 3 to 5.
- *Quantity.*—Abundant.
- *Shape.*—Oval with broad base and sharp apex. Serrations slight.
- *Size.*—Leaf averages 3½ inches long; terminal leaflet approximately 1½ inches long by ¾ inch wide.
- *Texture.*—Leathery.
- *Color.*—Medium to dark green.
- *Leaf stem.*—Lighter green than leaf and almost smooth.
- *Stipules.*—Small, basal, $\frac{1}{16}$ inch wide.

*The flower*

Bud:
- *Size.*—Average 1 inch long.
- *Shape.*—Long, pointed.
- *Color.*—White with slight tint of lemon. Opening to creamy white.

- *Peduncle.*—Light green, short, stiff and rigid. About 3 inches long.
- *Calyx and sepals.*—Smooth edged, early reflexing, rather simple with long narrow points.

Flower:
- *Borne.*—In large, well-branched clusters or trusses.
- *Size.*—Approximately 3½ inches across.
- *Form.*—Single, opening wide.
- *Color.*—White with highly contrasting anthers which are dull yellow in the opening flower but change to chocolate color when fully developed.
- *Petalage.*—Single, with 5 petals.
- *Fragrance.*—Strong.
- *Longevity.*—On bush, lasts 6 to 8 days after buds begin to expand. As cut flower, lasts well.

Petals:
- *Shape.*—Almost round.
- *Aspect.*—Silky.
- *Size.*—1¼ to 1½ inches in each dimension.
- *Color.*—Essentially white. Reverse of petals is slightly tinged with lemon and very pale pink.
- *Persistence.*—Drop after reaching maturity, leaving trusses clean.
- *Arrangement.*—In single row surrounding pistil and stamens.
- *Texture.*—Substantial and leathery.

Reproductive organs:
- *Pistils.*—Many, very tightly bunched, making a cushion. *Stigmas*—dull white. *Styles*—short and even.
- *Stamens.*—Many, surrounding pistils. *Anthers*—large; dull yellow at first but changing to chocolate color when fully developed. *Filaments*—red; uneven lengths.
- *Pollen.*—Yellow.
- *Ovaries.*—Ovoid.
- *Fruit.*—Light orange.

Having thus disclosed my invention, I claim:

The new and distinct variety of hybrid tea rose plant, substantially as herein shown and described, characterized particularly by its strong, compact growth; its large, well-branched bloom trusses; its continuous production of large quantities of flowers; and its flower of white petals with highly contrasting chocolate colored anthers supported by red filaments.

ALFRED KREBS.

No references cited.